United States Patent [19]

Owen et al.

[11] 4,170,648
[45] Oct. 9, 1979

[54] PHOSPHONOTHIOUREIDE ANTHELMINTICS

[75] Inventors: Ronald P. Owen, Warminster; George A. Miller, Glenside, both of Pa.; Charles M. Schneider, Cullowhee, N.C.

[73] Assignee: Rohm and Haas Company, Philadelphia, Pa.

[21] Appl. No.: 876,779

[22] Filed: Feb. 10, 1978

Related U.S. Application Data

[60] Division of Ser. No. 717,411, Aug. 24, 1976, Pat. No. 4,086,336, which is a continuation-in-part of Ser. No. 354,630, Apr. 25, 1973, abandoned, which is a continuation-in-part of Ser. No. 259,423, May 26, 1972, abandoned.

[51] Int. Cl.$^2$ .................... A01N 9/22; C07D 213/02; C07F 9/22
[52] U.S. Cl. ........................................ 424/200; 546/22
[58] Field of Search ................. 260/294.8 H, 294.8 K; 424/200; 546/22

[56] References Cited

U.S. PATENT DOCUMENTS

| | | | |
|---|---|---|---|
| 4,076,809 | 2/1976 | Weir et al. | 424/200 |
| 4,120,957 | 10/1978 | Weiler et al. | 424/204 |

*Primary Examiner*—Alan L. Rotman
*Attorney, Agent, or Firm*—Jacobs & Jacobs

[57] ABSTRACT

Aryl- and heterocyclic substituted phosphonothioureide compounds useful as anthelmintics.

11 Claims, No Drawings

PHOSPHONOTHIOUREIDE ANTHELMINTICS

This is a division of application Ser. No. 717,411 filed Aug. 24, 1976 now U.S. Pat. No. 4,086,336 which is a continuation-in-part of U.S. application Ser. No. 354,630 filed Apr. 25, 1973 now abandoned which is a continuation-in-part of U.S. application Ser. No. 259,423 filed May 26, 1972, now abandoned.

This invention relates to novel phosphorylthiourea compounds, to compositions containing them and to methods of employing them to control helminths in mammals and birds.

Helminthiasis is a disease affecting man and animals and is manifested by the infection of the host with parasites known as helminths. It is a widespread disease caused by a variety of helminths found in ruminants such as sheep, cattle and goats; equines such as horses and mules; domesticated small mammals such as dogs and cats; pigs; poultry and man. For example, tapeworms in sheep and cattle are represented by the genera Moniezia and Thysanesma; tapeworms in horses are commonly of the genera Anoplocephala and Paranoplocephala; important tapeworms of dogs and cats include the Dipylidium and Teania genera, as well as Echinoccocus in dogs; and poultry tapeworms include Davainea and Raillietina. In many, diphyllobothriasis, hymenolepiasis, dipylidiasis, taeniasis, echinococcosis and cysticerocosis, are important tapeworm infections most of which are transmitted by animals.

Roundworms found in sheep and cattle are of the genera Strongyloides, Oesophagostomum, Bunostomum, Haemonchus, Ostertagia, Trichostrongylus, Cooperia, Nematodirus and Chabertia. Similarly, the nematode genera commonly afflicting horses are Strongylus, Strongyloides, Trichonema, Parascaris and Oxyuris. Common roundworms of dogs and cats are Toxacaris; hookworms Ancylostoma and whipworms (Trichuris) afflict dogs as well. Some of the intestinal nematodes of man cause trichinosis, trichuriasis, strongyloidiasis, ancylostomiasis, oxyuriasis and ascariasis. The most economically important fluke of domestic sheep and cattle is *Fasciola hepatica;* this parasite bears some resemblance to the organism causing schistosomiasis in man.

The present invention provides a new class of anthelmintic compounds capable of ridding a host animal of one or more varieties of helminths as described above, especially tapeworms and roundworms.

These novel compounds have the following structural formula:

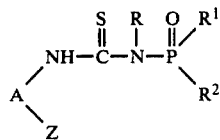

wherein A is a divalent arylene group such as phenylene, naphthylene, anthrylene, phenanthrylene and the like, or a divalent heterocyclic group, such as diazepinylene, pyridinylene, pyrimidylene, thienylene, furylene and the like, optionally substituted with (a) halo such as chloro, bromo and the like and preferably chloro; (b) cyano; (c) thiocyano; (d) carboxy; (e) nitro; (f) di-alkylamino of from 1 to 18 carbon atoms and preferably di-lower alkylamino of from 1 to 4 carbon atoms; (g) vicinal alkylene of from 2 to 6 carbon atoms, preferably trimethylene; (h) vicinal alkylenedioxy of from 1 to 4 carbon atoms, preferably methylenedioxy or (i) a radical of the formula: $R^3(X)_n$ wherein $R^3$ is an aliphatic of from 1 to 18 carbon atoms, preferably alkyl of from 1 to 8 carbon atoms, optionally substituted aryl, preferably aryl containing from 6 to 10 nuclear carbon atoms; optionally substituted heterocyclic, preferably one containing 5 or 6 nuclear atoms, which includes as hetero atoms, oxygen, sulfur, nitrogen and the like or any combination of these wherein the total number of hetero atoms does not exceed three; optionally substituted heterocyclicalkyl, wherein the heterocyclic group is as described above and the alkyl group preferably contains from 1 to 4 carbon atoms; X is oxo, thio, sulfinyl, sulfonyl or carbonyl and n is an integer of 0 to 1; R is hydrogen; $(C_1-C_{10})$ alkyl, preferably $(C_1-C_4)$ alkyl; $(C_1-C_{10})$ haloalkyl, preferably $(C_1-C_4)$ haloalkyl; $(C_3-C_6)$ cycloalkyl, preferably $(C_5-C_6)$ cycloalkyl; $(C_2-C_{11})$ alkoxyalkyl, preferably $(C_2-C_6)$ alkoxyalkyl; $(C_1-C_{10})$ cyanoalkyl, preferably $(C_1-C_4)$ cyanoalkyl; $(C_3-C_6)$ alkenyl, preferably $(C_3-C_4)$ alkenyl; $(C_3-C_6)$ haloalkenyl, preferably $(C_{3-C4})$ haloalkenyl; $(C_3-C_6)$ alkynyl, preferably $(C_3-C_4)$ alkynyl; $(C_3-C_6)$ haloalkynyl, preferably $(C_3-C_4)$ haloalkynyl; optionally substituted aralkyl of from 7 to 11 carbon atoms, preferably optionally substituted benzyl; or optionally substituted $(C_6-C_{10})$ aryl, preferably optionally substituted phenyl; $R^1$ is R', OR', $N(R')_2$ or SR' and $R^2$ is OR', $N(R')_2$ or SR' wherein R' is 3-aliphatic group of from 1 to 18 carbon atoms, preferably of from 1 to 8 carbon atoms or optionally substituted aryl, preferably containing from 6 to 10 nuclear carbon atoms, most preferably, optionally substituted phenyl; Z is a group selected from:

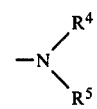

wherein $R^4$ and $R^5$ are hydrogen or aliphatic groups of from 1 to 18 carbon atoms, preferably of from 1 to 8 carbon atoms;

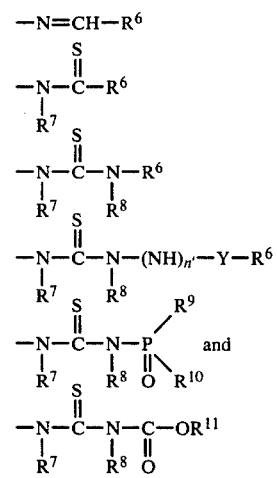

wherein $R^6$ is an aliphatic group of from 1 to 18 carbon atoms, preferably of from 1 to 8 carbon atoms; optionally substituted aryl, preferably containing from 6 to 10 nuclear carbon atoms, most preferably optionally substituted phenyl; optionally substituted heterocyclic group, preferably containing 5 or 6 nuclear atoms which includes as hetero atoms, oxygen, sulfur or nitrogen, or any combination of these wherein the total number of hetero atoms does not exceed three; an optionally substituted heterocyclic-alkyl group, wherein the heterocyclic group is as described above and the alkyl group preferably contains from 1 to 4 carbon atoms; $R^7$ and $R^8$ are independently hydrogen; $(C_1-C_{10})$ alkyl, preferably $(C_1-C_4)$ alkyl; $(C_1-C_{10})$ haloalkyl, preferably $(C_1-C_4)$ haloalkyl; $(C_3-C_6)$ cycloalkyl, preferably $(C_5-C_6)$ cycloalkyl; $(C_2-C_{11})$ alkoxyalkyl, preferably $(C_2-C_6)$ alkoxyalkyl; $(C_1-C_{10})$ cyanoalkyl, preferably $(C_1-C_4)$ cyanoalkyl; $(C_3-C_6)$ alkenyl, preferably $(C_3-C_4)$ alkenyl; $(C_3-C_6)$ haloalkenyl, preferably $(C_3-C_4)$ haloalkenyl; $(C_3-C_6)$ alkynyl, preferably $(C_3-C_4)$ alkynyl; $(C_3-C_6)$ haloalkynyl, preferably $(C_3-C_4)$ haloalkynyl; optionally substituted aralkyl of from 7 to 11 carbon atoms, preferably optionally substituted benzyl; or optionally substituted $(C_6-C_{10})$ aryl, preferably unsubstituted phenyl; $R^9$ is $R''$, $OR''$, $N(R'')_2$ or $SR''$ and $R^{10}$ is $R''$, $N(R'')_2$ or $SR''$ wherein $R''$ is an aliphatic group of from 1 to 18 carbon atoms, preferably of from 1 to 8 carbon atoms, or optionally substituted aryl preferably containing from 6 to 10 nuclear carbon atoms most preferably optionally substituted phenyl; provided that $R^9$ and $R^{10}$ are not simultaneously $R''$; $R^{11}$ is an aliphatic group of from 1 to 18 carbon atoms, preferably $(C_1-C_8)$ alkyl; or optionally substituted aryl, preferably containing from 6 to 10 nuclear carbon atoms, most preferably optionally substituted phenyl; n' is an integer of 0 to 1, preferably zero; and Y is carbonyl, sulfinyl or sulfonyl and the pharmaceutically acceptable metal salts, acid salts and metal salt complexes thereof.

The metal salts of this invention are the alkali, alkaline earth, and transition salts of the compounds of Formula I.

The metal salt complexes of this invention can be represented by the following formula which is presented for illustrative purposes only:

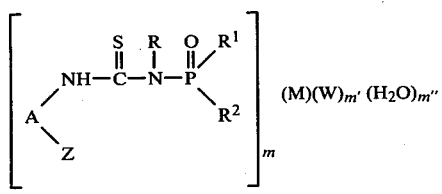

II wherein A, R, $R^1$, $R^2$ and Z are as defined for Formula I; M is a metal cation which is derived from group IIA, IIIA, IB, IIB, VIIB and VIII of the Periodic Table; W is an anion such as chloride, bromide, iodide, sulfate, bisulfate, phosphate, nitrate, perchlorate, carbonate, bicarbonate, hydroxide, acetate, oxalate, malate, citrate, and the like; m is an integer of 1 to 2; m' is an integer of 1 to 2 and m" is an integer of 0 to 4.

Among the compounds depicted by Formula II above, the preferred compounds are those wherein the metal salt cation is derived from transition metal such as copper, zinc, nickel, cobalt, tin, cadmium, manganese and the like or an alkaline earth metal such as calcium or magnesium and where the anion is chloride, bromide, nitrate, sulfate or hydroxide. The most preferred salts are those wherein the metal salt cation is derived from copper, zinc, nickel, cobalt, tin, cadmium or manganese and the anion is hydroxide.

The acid salts of this invention can be represented by the following formula which is presented for illustrative purposes only:

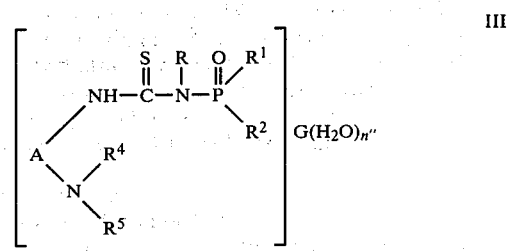

III wherein A, R, $R^1$, $R^2$, $R^4$ and $R^5$ are as defined for Formula I, G is a mineral acid, such as hydrochloric, hydrobromic, hydroiodic, sulfuric, phosphoric, nitric, perchloric, carbonic, and the like or an organic acid such as acetic, propionic, oxalic, malic, maleic, citric, p-toluenesulfonic, and the like; and n" is an integer of 0 to 4.

As used in the specification and claims, the terms "alkyl", "alkoxy", "alkenyl", "alkanoyl", "alkylthio", "alkylsulfinyl", "alkylsulfonyl", "dialkylamino", "aralkyl", and the like, are intended to include straight and branched chained groups.

The term "aliphatic group" is intended to include straight and branched chain unsubstituted and substituted aliphatic groups such as alkyl, alkenyl, substituted alkyl, for example, alkoxyalkyl, alkylthioalkyl, haloalkyl, cyanoalkyl, nitroalkyl; aralkyl; substituted aralkyl, for example, haloaralkyl, alkylaralkyl, alkoxyaralkyl, and the like; substituted alkenyl, for example, alkoxyalkenyl, alkylthioalkenyl, haloalkenyl, cyanoalkenyl, nitroalkenyl, alkenoxyalkenyl, and the like. The preferred aliphatic groups contain from 1 to 4 carbon atoms; the preferred aralkyls have from 6 to 10 nuclear carbon atoms.

Representative aliphatic unsubstituted and substituted groups include, for example, methyl, ethyl, propyl, butyl, sec-butyl, tert-butyl, pentyl, hexyl, heptyl, octyl, sec-butyl, tert-octyl, nonyl, decyl, undecyl, dodecyl, octadecyl, ethoxyethyl, methylthiobutyl, chloroethyl, trifluoromethyl, trichloropropyl, cyanoethyl, nitrodecyl, allyl, vinyl, oleyl, stearyl, methoxyallyl, chlorovinyl, methylthiopentenyl, cyanoallyl, nitrostearyl, benzyl, phenethyl, α-methylphenethyl, 3,4-dichlorobenzyl, 4-methylbenzyl and the like.

The term "optionally substituted", when used to modify terms such as "aromatic", "aralkyl", "phenyl", "napthyl", "benzyl", "aryl", "heterocyclic", "heterocyclicalkyl", and the like, indicates that these groups can be unsubstituted or substituted with one or more substituents, preferably with two substituents. Examples of such substituents include halo, nitro, cyano, $(C_1-C_4)$ alkyl, $C_1-C_4$ (haloalkyl), $(C_1-C_4)$ alkoxy, $(C_1-C_4)$ alkylthio, $(C_1-C_4)$ alkylsulfinyl, $(C_1-C_4)$ alkylsulfonyl, $(C_1-C_4)$ alkylcarbonyl, di$(C_1-C_4)$ alkylamino, $(C_3-C_4)$ alkenyl, $(C_3-C_4)$ alkenylthio, $(C_3-C_4)$ alkenylsulfinyl, $(C_3-C_4)$ alkenylsulfonyl, azidosulfinyl, azidosulfonyl, cyanothio, halosulfinyl, halosulfonyl, halothio, vicinal $(C_2-C_6)$ alkylene, and the like.

The preferred substituents include halo, preferably chloro, nitro, cyano, $(C_1-C_4)$ haloalkyl, $(C_1-C_4)$ alkyl, $(C_1-C_4)$ alkoxy and di$(C_1-C_4)$ alkylamino.

The preferred compounds of this invention can be represented by the following formula:

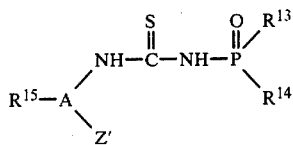

wherein A is phenylene, naphthylene or phenanthrylene or pyridinylene; $R^{13}$ and $R^{14}$ are the same or different radicals selected from $OR_1'$, $N(R_1')_2$ or $SR_1'$ wherein $R_1'$ is $(C_1-C_4)$ alkyl, $(C_2-C_6)$ alkoxylalkyl, $(C_1-C_4)$ haloalkyl, $(C_3-C_4)$ alkenyl or phenyl; $R^{15}$ represents from 1 to 4 and preferably from 1 to 2 substituents when A is phenylene or pyridinylene and $R^4$ represents from 1 to 6 and preferably from 1 to 2 substituents when A is napthylene or phenanthrylene, which substituents can be hydrogen; $(C_1-C_4)$ alkyl; $(C_1-C_4)$ alkoxy; $(C_3-C_4)$ alkenyl; halogen; nitro; carboxy; or a benzoyl, phenylthio, phenylsulfinyl or phenylsulfonyl group and preferably benzoyl provided that $R^{15}$ does not represent more than one of these groups and Z is a group of the formula:

$R^{16}$ is hydrogen; $(C_1-C_6)$ alkyl and preferably $(C_1-C_4)$ alkyl; $(C_1-C_6)$ haloalkyl, and preferably, $(C_1-C_4)$ haloalkyl; $(C_3-C_6)$ alkenyl, and preferably, $(C_3-C_4)$ alkenyl; $(C_2-C_8)$ alkoxyalkyl, and preferably, $(C_2-C_4)$ alkoxyalkyl; optionally substituted aralkyl of up to 11 carbon atoms, and preferably, optionally substituted benzyl or optionally substituted $(C_6-C_{10})$ aryl, and preferably, optionally substituted phenyl,

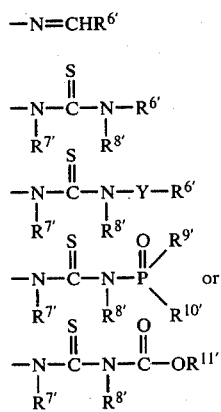

wherein $R^{6'}$ is $(C_1-C_4)$ alkyl; $(C_1-C_4)$ haloalkyl; optionally substituted aralkyl of up to 11 carbon atoms, and preferably, optionally substituted benzyl; optionally substituted $(C_6-C_{10})$ aryl, and preferably, optionally substituted phenyl; an optionally substituted heterocyclic containing 5 or 6 nuclear members, which includes as hetero atoms, oxygen, sulfur, or nitrogen, or any combination of these wherein the total number of hetero atoms does not exceed three, preferably unsubstituted thiophene, pyridine, or furan; or an optionally substituted heterocyclic alkyl group wherein the heterocyclic group is as described above and the alkyl group preferably contains 1 to 4 carbon atoms; $R^{7'}$ and $R^{8'}$ are independent hydrogen; $(C_1-C_4)$ alkyl; $(C_3-C_4)$ alkenyl; $(C_2-C_4)$ alkoxyalkyl or optionally substituted aralkyl of up to 11 carbon atoms, and preferably, optionally substituted benzyl; $R^{9'}$ is $OR_1''$, $SR_1''$ or $N(R_1'')_2$ and $R^{10'}$ is $SR_1''$ or $N(R_1'')_2$, wherein $R_1''$ is $(C_1-C_4)$ alkyl, $(C_2-C_6)$ alkoxyalkyl, $(C_1-C_4)$ haloalkyl, $(C_3-C_4)$ alkenyl or phenyl, $R^{11'}$ is $(C_1-C_8)$ alkyl, preferably, $(C_1-C_4)$ alkyl or optionally substituted phenyl, preferably unsubstituted phenyl; and Y is carbonyl, sulfinyl or sulfonyl, preferably, carbonyl or sulfonyl, and the pharmaceutically acceptable metal salts, acid salts, and metal salt complexes thereof.

The most preferred compounds of this invention are especially effective as anthelmintics and can be represented by a formula selected from:

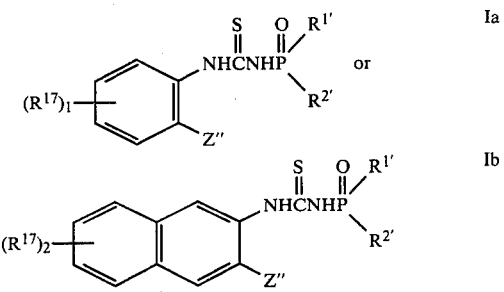

wherein $R^{1'}$ or $OR_2'$ and $R^{2'}$ is $OR_2'$ or $SR_2'$ wherein $R_{2'}$ is $(C_1-C_4)$ alkyl, $(C_1-C_4)$ haloalkyl or phenyl; $R^{17}$ is hydrogen, $(C_1-C_4)$ alkyl; $(C_1-C_4)$ alkoxy; halo; benzoyl or carboxy; $Z''$ is a group of the formula: $NH_2$, $NHR^{18}$ wherein $R^{18}$ is $(C_1-C_8)$ alkyl, preferably $(C_1-C_4)$ alkyl; $(C_2-C_8)$ alkoxyalkyl, preferably $(C_2-C_4)$ alkoxyalkyl; $(C_3-C_8)$ alkenyl, preferably $(C_3-C_4)$ alkenyl, or benzyl, optionally substituted with one to two substituents selected from $(C_1-C_4)$ alkyl, $(C_1-C_4)$ alkoxy, $(C_1-C_4)$ haloalkyl, di$(C_1-C_4)$ alkylamino, halo, nitro or cyano, preferably, halo, and most preferably, chloro; $—N=CHR^{19}$ wherein $R^{19}$ is phenyl, optionally substituted with one to two substituents selected from $(C_1-C_4)$ alkyl, $(C_1-C_4)$ alkoxy, $(C_1-C_4)$ haloalkyl, di-$(C_1-C_4)$ alkylamino, halo, nitro or cyano, preferably, halo, and most preferably, chloro;

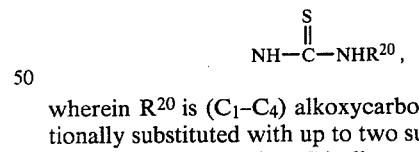

wherein $R^{20}$ is $(C_1-C_4)$ alkoxycarbonyl or phenyl, optionally substituted with up to two substituents selected from $(C_1-C_4)$ alkyl, $(C_1-C_4)$ alkoxy, $(C_1-C_4)$ haloalkyl, di-$(C_1-C_4)$ alkylamino, halogen, nitro or cyano, preferably, cyano;

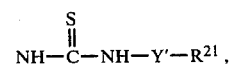

wherein $R^{21}$ is $(C_1-C_4)$ alkyl, $(C_1-C_4)$ haloalkyl, $(C_2-C_4)$ allyl or phenyl optionally substituted with one to two substituents selected from $(C_1-C_4)$ alkyl, $(C_1-C_4)$ alkoxy, $(C_1-C_4)$ haloalkyl, di-$(C_1-C_4)$ alkylamino, halo, nitro and cyano, preferably halo, most preferably, chloro and $Y'$ is carbonyl or sulfonyl and the pharmaceutically acceptable metal salts, acid salts and metal salt complexes thereof.

The compounds of the present invention are prepared by various methods, several of which are disclosed herein. Certain compounds of this invention can also be prepared according to the procedure disclosed in U.S. Pat. No. 3,845,176 which is incorporated herein by reference. This patent discloses a multi-step process with requires only a single reaction vessel purification work-up. The process disclosed comprises the following steps:

(1) reacting a thiocyanate salt and a chlorophosphate in an appropriate solvent to form the phosphonoisothiocyanate;

(2) adding an o-phenylenediamine to the phosphonoisothiocyanate to form the phosphonothioureido-2-amino benzene compound;

(3) adding an isothiocyanate to the product formed in (2) to obtain the final product and (4) recovering the product by physical separation and washing with water to remove the salt formed.

It has now been found that a higher yield and greater purity of products can be obtained if in the above process:

(a) step 1 is carried out at about 50° C.;
(b) step 2 is carried out at about 0° C.;
(c) step 3 is carried out at about 0° C.;
held at that temperature for about one hour and then warmed to about 20° C. for one hour and (d) after step 4, and additional purification step is performed as described in the following paragraph.

The final product is suspended in water to which is added two equivalents of an alkali hydroxide, e.g., sodium hydroxide, to form the dialkali salt. The suspension is extracted with a solvent non-miscible with water, for example, either or ethyl acetate. The extract is discarded and the aqueous phase of the dialkali salt is made acidic with a mineral acid, for example, hydrochloric acid, to a pH of from 1 to 5. The purified product precipitates and is collected by vacuum filtration.

The following general procedures are given by way of illustration and are not to be considered as limitations of the present invention. Many variations of this invention are possible without departing from the spirit or scope of the invention. The first five sections of the general procedures deal with the preparation of starting materials necessary to prepare compounds of this invention. All other starting materials used in the preparation of the compounds of this invention are known compounds or are readily prepared by methods known to those skilled in the art. All temperatures are in degrees Celsius.

PREPARATION OF STARTING MATERIALS

Procedure 1—Synthesis of Disubstituted Phosphoryl-Isothiocyanates

An appropriate disubstituted chlorophosphate (1 mole) is added dropwise to an ice-cooled solution of potassium thiocyanate (1.1 mole) in 500 ml. of dry acetone. The suspension which forms is stirred at room temperature for two days and is concentrated in vacuo. The residue is suspended in 300 ml. benzene and washed with cold water until the washings record a pH of 5. The benzene solution is dried over magnesium sulfate and then filtered and concentrated in vacuo to afford a yellow-orange liquid. The infrared spectrum of these materials shows a strong isothiocyanate band a 4.6–5.1. microns.

Table I presents the results of eight such syntheses.

TABLE I $$\begin{array}{c} Y \\ \diagdown \\ Y' \end{array} \!\!\! \begin{array}{c} O \\ \| \\ P \end{array} \!\! N\!\!=\!\!C\!\!=\!\!S$$

| Example No. | Y | Y' | Yield |
|---|---|---|---|
| 1 | C$_2$H$_5$O— | C$_2$H$_5$O— | 65% |
| 2 | CH$_3$O— | CH$_3$O— | 18.5% |
| 3 | iso-C$_3$H$_7$O— | iso-C$_3$H$_7$O— | 75% |
| 4 | ⌬—O— | ⌬—O— | 36% |
| 5 | (CH$_3$)$_2$N— | (CH$_3$)$_2$N— | 41% |
| 6 | CH$_3$S— | C$_2$H$_5$O— | 45.6% |
| 7 | C$_2$H$_5$S— | C$_2$H$_5$O— | 24% |
| 8 | C$_3$H$_7$S— | C$_2$H$_5$O— | 76.4% |

Procedure 2—Synthesis of Disubstituted Phosphorylthio-carbamoyl chlorides

To a solution of diethylmethylamidophosphate (16.7 g.; 0.1 mole) in glyme (100 ml.) is added 57% of sodium hydride (4.04 g.; 0.1 mole) (oil dispersed). The mixture is stirred at room temperature for three hours and is added dropwise to an ice-cooled solution of 12.5% thiophosgene in benzene (11.5 g.; 0.1 mole). The resultant suspension is stirred at room temperature overnight and is vacuum filtered through celite. The filtrate is concentrated in vacuo to afford the product.

Procedure 3—Synthesis of Aryl- or Alkylsulfonyliso-thiocyanates

Step A—To a solution of an aryl- or alkylsulfonamide (1 mole) and carbon disulfide (1 mole) in dry dimethylformamide (50 ml.) is added potassium hydroxide as pellets. The suspension which forms is stirred at room temperature for two hours, after which additional potassium hydroxide (1 mole) is added. The temperature of the exothermic reaction is maintained at 35° with ice cooling. A thick suspension forms which is stirred for 24 hours at room temperature and then vacuum filtered. Table II presents results of three syntheses.

Step B—To the dipotassium salt of Step A (0.48 mole) is added phosgene (0.5 mole) in 12.5% benzene solution with ice cooling and stirring. The resultant suspension is stirred at room temperature for 24 hours under anhydrous conditions and then filtered. The potassium chloride residue is washed with ether (3×100 ml.), and the filtrate and washings are concentrated in vacuo. The yellow-orange oil obtained is of high purity. The infrared spectrum shows an isothiocyanate band at 4.9–5.4 microns. Table III presents the results of three such syntheses.

TABLE II $$R\!-\!SO_2N\!\!=\!\!C \begin{array}{c} \diagup SK \\ \diagdown SK \end{array}$$

| Ex. No. | R | Yield | Melting Point (°C.) |
|---|---|---|---|
| 9 | CH$_3$ | 95% | 281° (decomposed) |
| 10 | CH$_3$CH$_2$— | 80% | 225°–229° (decomposed) |

TABLE II-continued $$R-SO_2N-C \begin{smallmatrix} SK \\ \\ SK \end{smallmatrix}$$

| Ex. No. | R | Yield | Melting Point (°C.) |
|---|---|---|---|
| 11 | CH₃—⟨phenyl⟩— | 70% | 242°–248° (decomposed) |

TABLE III $$R-SO_2N=C=S$$

| Ex. No. | R | Yield |
|---|---|---|
| 12 | $CH_3-$ | 95% |
| 13 | $CH_3CH_2-$ | 91% |
| 14 | $CH_3-\text{⟨phenyl⟩}-$ | 89% |

The aralkyl, heterocyclic, and heterocyclic-alkyl sulfonylisothiocyanates can be prepared in an analogous manner.

Procedure 4—Preparation of Arylsulfonylthiocarbamoyl Chlorides

To a solution of an appropriate sulfonamide in a suitable solvent, for example, an aprotic solvent and especially glyme, is added an equimolar quantity of sodium hydride (oil dispension) with stirring at room temperature. To the resultant suspension, cooled in an ice bath, is added with stirring, a solution of a molar excess of thiophosgene in benzene. The suspension is stirred overnight, the precipitate is filtered and the filtrate is concentrated in vacuo to afford the desired product.

The alkyl, aralkyl, heterocyclic and heterocyclic-alkyl sulfonylthiocarbamoyl chlorides can be prepared in a manner analogous to that of Procedure 4.

Procedure 5—Synthesis of Alkanoyl or Aroylisothio-cyanates

An appropriate alkanoyl or aroyl chloride (0.25 mole) is added to a benzene suspension of lead thiocyanate (97 g.; 0.3 mole). The mixture is refluxed and stirred for 24 hours and then vacuum filtered through diatomaceous earth. The filtrate is concentrated in vacuo and is vacuum distilled. The infrared spectrum of these materials shows strong isothiocyanate bands at 4.8–5.2 microns and

bands at 5.8–5.9 microns.

Table IV presents the results of six such syntheses.

TABLE IV $$\overset{O}{\underset{\|}{R C N}}=C=S$$

| Ex. No. | R | Yield | BP/mm of H₉ |
|---|---|---|---|
| 15 | $CH_3-$ | 40% | 57°/32 mm |
| 16 | $CH_3CH_2-$ | 54% | 81°/60 mm |
| 17 | $ClCH_2-$ | 35% | 98°/50 mm |
| 18 | ⟨phenyl⟩— | 40% | 90°/1.3 mm |
| 19 | $CH_3-$⟨phenyl⟩— | 60% | 88°/0.4 mm |
| 20 | $CCl_3-$⟨phenyl⟩— | 60% | 125°/0.2 mm (also melting point:61°–65°) |

The aralkanoyl, heterocyclic-carbonyl and heterocyclicalkylcarbonyl isothiocyanates can be prepared in a manner analogous to that of Procedure 5.

FINAL PRODUCTS

Procedure 6—Synthesis of 1-(3-Disubstituted Phosphorylthioureido)-2-Aminobenzene Compounds To a solution of the desired ortho arylene diamine or ortho heterocyclic diamine in an aprotic solvent is added one equivalent of the desired phosphoryl isothiocyanate (exothermic reaction). The reaction mixture is maintained at room temperature for the reaction period indicated in Table V and a precipitate is formed. The product is isolated by vacuum filtration and is identified by elemental analysis and infrared spectrum. Table V presents the results of 19 such syntheses.

TABLE V $$A \begin{smallmatrix} NH-\overset{S}{\underset{\|}{C}}-NH-\overset{O}{\underset{\|}{P}}\diagup\overset{R^2}{\diagdown R^3} \\ \\ NH-R^1 \end{smallmatrix}$$

| Ex. No. | A | R¹ | R² | R³ | Melting Point |
|---|---|---|---|---|---|
| 21 | ⟨benzene ring⟩ | H | $-OC_2H_5$ | $-OC_2H_5$ | 135°–138° dec. |
| 22 | ⟨benzene ring⟩ | H | $-OC_3H_7$-iso | $-OC_3H_7$-iso | 116°–117.5° dec. |

TABLE V-continued

| # | Aryl | R | X | Y | mp |
|---|------|---|---|---|-----|
| 23 | 4-benzoyl-3-methylphenyl (benzophenone derivative) | H | —OC₂H₅ | —OC₂H₅ | 155° dec. |
| 24 | o-tolyl | CH₃ | —OC₂H₅ | —OC₂H₅ | 110°–114° dec. |
| 25 | o-tolyl | —C₄H₉ | —OC₂H₅ | —OC₂H₅ | 78°–80° dec. |
| 26 | o-tolyl | —CH₂CH=CH₂ | —OC₂H₅ | —OC₂H₅ | 69°–72° dec. |
| 27 | o-tolyl | —CH₂—C₆H₅ | —OC₂H₅ | —OC₂H₅ | 115°–118° dec. |
| 28 | o-tolyl | —(CH₂)₃OCH₃ | —OC₂H₅ | —OC₂H₅ | 76°–79° dec. |
| 29 | o-tolyl | H | —OC₂H₅ | —SC₂H₅ | 121°–124° slight dec. |
| 30 | o-tolyl | H | —OC₂H₅ | —SCH₃ | 131°–133° dec. |
| 31 | o-tolyl | H | —OC₂H₅ | —SC₃H₇ | 85°–93° |
| 32 | o-tolyl | H | —N(CH₃)₂ | —N(CH₃)₂ | 136°–137° |
| 33 | o-tolyl | H | —O(CH₂)₂Cl | —O(CH₂)₂Cl | 111°–120° |
| 34 | 4-carboxy-3-methylphenyl | H | —OC₂H₅ | —OC₂H₅ | 167° dec. |
| 35 | o-tolyl | H | —OC₂H₅ | —SC₃H₇-iso | 104°–108° dec. |
| 36 | o-tolyl | H | —OC₂H₅ | —SC₄H₉-iso | 88°–90° |
| 37 | 2,3-naphthyl | H | —OC₂H₅ | —OC₂H₅ | 148°–151° dec. |

TABLE V-continued

| | | | | | |
|---|---|---|---|---|---|
| 38 | (phenanthrene structure) | H | —OC$_2$H$_5$ | —OC$_2$H$_5$ | 175°–177° dec. |
| 39 | (pyridine structure) | H | —OC$_2$H$_5$ | —OC$_2$H$_5$ | 133°–136.5° dec. |

REACTION CONDITIONS

| Example No. | Diamine (mole) | Isothiocyanate (mole) | Reaction Solvent | Reaction Time | Precipitating Solvent |
|---|---|---|---|---|---|
| 21 | 0.186 | 0.186 | glyme | 18 hours | none |
| 22 | 0.186 | 0.186 | glyme | 18 hours | ether |
| 23 | 0.03 | 0.03 | acetone | 2 hours | none |
| 24 | 0.02 | 0.02 | glyme | 24 hours | water |
| 25 | 0.02 | 0.02 | glyme | 6 days | water |
| 26 | 0.01 | 0.01 | glyme | 1 week | water |
| 27 | 0.02 | 0.02 | glyme | 2 hours | none |
| 28 | 0.0205 | 0.0205 | ethyl acetate | 2 hours | hexane |
| 29 | 0.0118 | 0.0118 | glyme | 24 hours | water |
| 30 | 0.01 | 0.01 | glyme | 18 hours | water |
| 31 | 0.01 | 0.01 | glyme | 18 hours | water |
| 32 | 0.02 | 0.02 | glyme | 3 hours | none |
| 33 | 0.076 | 0.076 | glyme | 2 hours | none |
| 34 | 0.005 | 0.01 | acetone | several hours | none |
| 35 | 0.0178 | 0.0178 | glyme | 3 hours | ether |
| 36 | 0.01 | 0.01 | glyme | 18 hours | water |
| 37 | 0.01 | 0.01 | glyme | 18 hours | none |
| 38 | 0.005 | 0.005 | glyme | 4 days | none |
| 39 | 0.01 | 0.01 | glyme | 15 minutes | none3 |

Procedure 7—Synthesis of 1-(3-disubstituted phosphorylthioureido)-2-(3-substituted sulfonyl or carbonylthioureido or 3-disubstituted phosphorylthioureido)benzene compounds To a mixture of the appropriate arylenediamine or 1-(3-disubstituted phosphorylthioureido)-2-amino benzene compound in an appropriate solvent (see Table VI) there is added the appropriate isothiocyanate (see Table VI). The reaction mixture is maintained at room temperature for the reaction period indicated in Table VI and the precipitated product (precipitated by the solvent indicated in Table VI) is isolated by vacuum filtration. The product is identified by elemental analysis and infrared spectrum.

Twenty compounds prepared in a manner analogous to that of Procedure 7 are presented in Table VI.

TABLE VI $$X-\text{(benzene ring)}-\begin{array}{c} NHC(S)NHP(O)(Y)(Y') \\ NHC(S)NHR \end{array}$$

| Example No. | Y | Y' | R | X | Melting Point (°C.) |
|---|---|---|---|---|---|
| 1 | C$_2$H$_5$O— | C$_2$H$_5$O— | CH$_3$SO$_2$— | H | 162–163 dec. |
| 2 | C$_2$H$_5$O— | C$_2$H$_5$O— | C$_2$H$_5$SO$_2$— | H | 148–151 dec. |
| 3 | C$_3$H$_7$O-iso- | C$_3$H$_7$O-iso- | CH$_3$SO$_2$— | H | 165–165.5 dec. |
| 4 | C$_2$H$_5$O— | C$_2$H$_5$O— | CH$_3$SO$_2$— | Cl | 168 dec. |
| 5 | C$_2$H$_5$O— | C$_2$H$_5$O— | CH$_3$C(O)— | H | 157.5–159 |
| 6 | C$_2$H$_5$O— | C$_2$H$_5$O— | C$_2$H$_5$C(O)— | H | 155–156.5 |
| 7 | Cl(CH$_2$)$_2$O— | Cl(CH$_2$)$_2$O— | CH$_3$C(O)— | H | 162–164 |
| 8 | C$_2$H$_5$O— | C$_2$H$_5$O— | ClCH$_2$C(O)— | H | 129–130 dec. |

TABLE VI-continued

| Ex. No. | | | | | |
|---|---|---|---|---|---|
| 9 | $C_2H_5O-$ | $C_2H_5O-$ | phenyl-C(=O)- | H | 175-176 dec. |
| 10 | $C_2H_5O-$ | $C_2H_5O-$ | phenyl-C(=O)- | H | 160-162.5 dec. |
| 11 | $C_2H_5O-$ | $C_2H_5O-$ | phenyl-C(=O)- | H | 130.5-132.5 dec. |
| 12 | $C_3H_7S$-iso- | $C_2H_5O-$ | $-P(=O)(SC_3H_7\text{-iso})(OC_2H_5)$ | H | 131-132 dec. |
| 13 | $C_4H_9S$-sec- | $C_2H_5O-$ | $-P(=O)(SC_4H_9\text{-sec})(OC_2H_5)$ | H | 65 |
| 14 | $C_3H_7S$-iso- | $C_2H_5O-$ | $-P(=O)(OC_2H_5)(OC_2H_5)$ | H | 123-125 |
| 15 | $CH_3S-$ | $C_2H_5O-$ | $-P(=O)(N(CH_3)_2)(N(CH_3)_2)$ | H | 127-129 dec. |
| 16 | $C_2H_5O-$ | $C_2H_5O-$ | $-P(=O)(N(CH_3)_2)(N(CH_3)_2)$ | H | 119-120 dec. |
| 17 | $C_2H_5O-$ | $C_2H_5O-$ | $-P(=O)(SC_3H_7\text{-iso})(OC_2H_5)$ | H | 129-131 dec. |
| 18 | $C_3H_7S$-n- | $C_2H_5O-$ | $-P(=O)(SC_3H_7\text{-n})(OC_2H_5)$ | H | 137-138 dec. |
| 19 | $CH_3S-$ | $C_2H_5O-$ | $-SO_2CH_3$ | H | 149-150 dec. |
| 20 | $C_2H_5O-$ | $C_2H_5O-$ | 2-thienyl-C(=O)- | H | 170.5-173 dec. |

REACTION CONDITIONS

| Ex. No. | Yield | M.P. (°C.) | Reaction Time | Diamine or 2-Aminothiourea (mole) | Isothiocyanate (mole) | Solvent | Precipitating Solvent |
|---|---|---|---|---|---|---|---|
| 1 | 97% | 162-163 dec. | 30 min. | 0.2 | 0.3 | glyme | none |
| 2 | 27% | 148-151 dec. | 18 hr. | 0.2 | 0.3 | glyme | none |
| 3 | 72% | 165-165.5 dec. | 15 min. | 0.2 | 0.3 | glyme | none |
| 4 | 84% | 168 dec. | 30 min. | 0.2 | 0.3 | glyme | none |
| 5 | 74% | 157.5-159 | 30 min. | 0.1 | 0.03 | glyme | none |
| 6 | 84% | 155-156.5 | 15 min. | 0.02 | 0.04 | glyme | none |
| 7 | 91% | 162-164 | 3 hr. | 0.1 | 0.03 | glyme | none |
| 8 | 17.8% | 129-130 dec. | 2+ hr. | 0.02 | 0.02 | glyme | none |
| 9 | 81% | 175-176 dec. | 25 hr. | 0.02 | 0.04 | glyme | none |
| 10 | 77% | 160-162.5 dec. | 5 min | 0.01 | 0.01 | glyme | none |
| 11 | 31% | 130.5-132.5 dec. | 5 hr. | 0.01 | 0.01 | glyme | none |
| 12 | 29% | 131-132 dec. | 3 hr. | 0.0089 (diamine) | 0.0178 | glyme | ether |
| 13 | 14% | 65 | 8 days | 0.005 (diamine) | 0.01 | glyme | water |
| 14 | 68% | 123-125 | 1 hr. | 0.0129 | 0.0129 | acetonitrile | none |
| 15 | 14% | 127-129 dec. | 6 hr. | 0.0056 (diamine) | 0.0112 | acetone | ether |
| 16 | 49% | 119-120 dec. | 18 hr. | 0.02 | 0.02 | acetonitrile | ether |
| 17 | 45% | 129-131 dec. | 18 hr. | 0.02 | 0.02 | acetonitrile | ether |

TABLE VI-continued

| 18 | 6% | 137–138 dec. | 3 days | 0.03 (diamine) | 0.03 | glyme | none |
| 19 | 46% | 149–150 dec. | 2 hr. | 0.05 | 0.15 | glyme | none |
| 20 | 76.5% | 170.5–173 dec. | 15 min. | 0.01 | 0.15 | glyme | none |

Procedure 8—Synthesis of 1-(3-Disubstituted phosphorylthioureido)-2-substituted thioamidobenzene compounds Step A—To a mixture of a 1-(3-disubstituted phosphorylthioureido)-2-aminobenzene or heterocyclicamine compound in an aprotic solvent, is added one equivalent of an appropriate acylating agent (isothiocyanate, thioacid halide, or thiocarbamoyl chloride). The reaction mixture is maintained at room temperature for a reaction period of from two hours to three days. The desired product can be separated from the reaction mixture by conventional means such as by fractional crystallization, extraction or the like.

Step B—To a suspension of the desired monoacylated arylene or heterocyclic diamine in an aprotic solvent is added the appropriate phosphorylisothiocyanate. In some cases, it may be necessary to briefly heat the reaction mixture to initiate the reaction. The reaction mixture is maintained at room temperature until the reaction is essentially complete. The desired product can be separated from the reaction mixture by conventional means, such as by fractional crystallization, extraction or the like.

The following compound is made according to Procedure A.

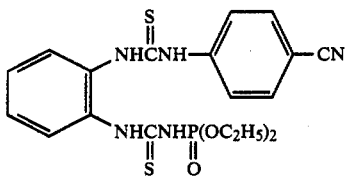

Procedure 9—Synthesis of 1-(3-Disubstituted phosphorylthioureido)-2-[iminophenyl (or substituted phenyl)methyl]benzene compounds To an ice cooled suspension of 0.01 mole of an appropriate 1-(3-disubstituted phosphorylthioureido)-2-aminobenzene or aminoheterocyclic compound in 20 ml. of methanol, there is added 0.01 mole of an appropriately substituted or unsubstituted benzaldehyde. The mixture is stirred at 0° C. for one to two hours and is vacuum filtered. The filter cake is dried to afford the desired product.

Table VII presents the results of two such syntheses.

TABLE VII

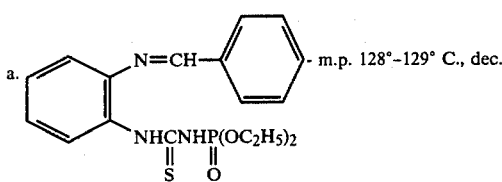
a. - m.p. 128°–129° C., dec.

-continued
TABLE VII

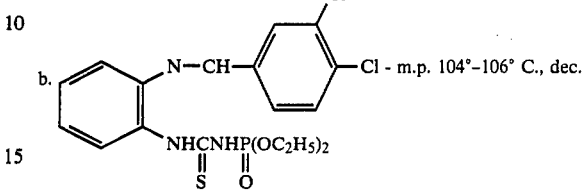
b. - m.p. 104°–106° C., dec.

The alkali and alkaline earth metal salts of this invention are prepared by adding an alkali or alkaline earth metal hydroxide or hydride to a suspension of the appropriate phosphoramidate in a suitable solvent, stirring the mixture until a soluton forms, and then either freeze drying the solution or concentrating it in vacuo at room temperature and drying the residue in a vacuum oven at room temperature.

The transition metal salts of this invention are prepared by adding a transition metal salt, such as zinc chloride, to the alkali or alkaline earth metal salt in the presence of an appropriate solvent.

The acid salts of this invention are prepared by reacting a phosphoramidate of Formula III above in glyme, with an equivalent or excess of an appropriate mineral or organic acid at a temperature in the range of from about 0° to about 50°. The reaction mixture is stirred at room temperature for about 2 to about 18 hours. The product is separated from the reaction mixture by conventional means such as by fractional crystallization, chromatography, extraction or the like.

The metal salt complexes of this invention are prepared by reaction, in an aqueous or alcohol medium, a phosphoramidate of this invention, or alkali metal salt thereof, with an equivalent or excess amount of a metal cation derived from Group IIA, IIIA, IB, IIB, VIIB or VIII of the Periodic Table and then filtering the precipitate to afford the desired product.

All of the compounds described in this application can be used as anthelmintics for combatting infections in avians, cats, dogs, sheep, porcine, bovine, equine and man. As set forth below, these compounds can be administered in liquid or preferably tablet form to the host.

The compounds of this invention may be combined advantageously with other anthelmintics. Since the prepared compounds have activity not found in certain other anthelmintics such as thiabendazole, phenothiazine, piperazine, tetramisole, pyrantel, niclosamide, bunamidine, etc. combinations of the present compounds and other anthelmintics would possess clinical utility. Appropriate dosage forms containing a plurality of anthelmintically active compounds are accordingly contemplated by the present invention.

For use against species of roundworms as well as tapeworms, the preferred compounds are most desirably administered between about 12 and 100 mg./kg.; while for use against tapeworms only, the effective dose may be somewhat lower, e.g., 3 to 50 mg./kg.

A wide variety of formulations of conventional pharmaceutical excipients may be employed. By way of illustration, Examples I and II present formulations for tablets and chewable tablets, respectively:

EXAMPLE 1

A table of the following composition is formulated:

| Active Compound | 220 mg. |
|---|---|
| Lactose | 53.23 mg. |
| Magnesium Aluminum Silicate Gel | 2.24 mg. |
| Starch | 13.13 mg. |
| Calcium Stearate | 0.65 mg. |
| Microcrystalline Cellulose | 35.75 mg. |
| TOTAL | 325 mg. |

A granulation, containing water by the use of magnesium aluminum silicate and starch in the form of pastes, is tableted to form flat level, double or quarter scored, uncoated tablets, of 6 to 9 S. C. A. hardness. The appropriate number (and fraction) of tablets is administered to the host, e.g., one tablet per 20 lbs. body weight.

EXAMPLE II

An alternative formulation is in the form of a palatable chewable tablet. Each chewable tablet contains:

| Active Compound | 110 mg. |
|---|---|
| Dried Fish Meal | 1027 mg. |
| Dried Liver Powder, Bovine | 1027 mg. |
| Soybean Oil Meal | 97 mg. |
| Cane Sugar | 239 mg. |
| TOTAL | 2500 mg. |

The present invention may be embodied in other specific forms without departure from the spirit or essential attributes thereof and, accordingly, reference should be made to the appended claims, rather than to the foregoing specification as indicating the scope of the invention.

What is claimed is:

1. A compound of the formula:

$$\underset{A}{\overset{}{\underset{Z}{\diagdown}}} NH - \overset{S}{\overset{\|}{C}} - \overset{R}{\underset{|}{N}} - \overset{O}{\overset{\|}{P}} \overset{R^1}{\underset{R^2}{\diagup}}$$

or a pharmaceutically acceptable metal salt, acid salt or metal salt complex thereof wherein A is pyridinylene unsubstituted or substituted by one or two members selected from the group consisting of halo, cyano, thiocyano, carboxy, nitro, di-lower alkylamino, vicinal alkylene of 2 to 6 carbon atoms, vicinal alkylenedioxy of 1 to 4 carbon atoms or a moiety of the formula $R^3(X)_n$ wherein $R^3$ is alkyl of 1 to 8 carbon atoms or aryl of 6 to 10 carbon atoms;

X is oxo, thio, sulfinyl, sulfonyl or carbonyl;

n is zero or 1;

R is hydrogen, alkyl of 1 to 4 carbon atoms, haloalkyl of 1 to 4 carbon atoms, cycloalkyl of 5 or 6 carbon atoms, alkoxyalkyl of 2 to 6 carbon atoms, cyanoalkyl of 1 to 4 carbon atoms, alkenyl of 3 or 4 carbon atoms, haloalkenyl of 3 or 4 carbon atoms, alkynyl of 3 or 4 carbon atoms, haloalkynyl of 3 or 4 carbon atoms, benzyl or phenyl;

$R^1$ is R', OR', N(R')$_2$ or SR' and $R^2$ is OR', N(R')$_2$ or SR' wherein R' is an aliphatic moiety of 1 to 8 carbon atoms or phenyl;

$$Z \text{ is } -N \diagup_{R^5}^{R^4}$$

wherein $R^4$ and $R^5$ are each hydrogen or an aliphatic moiety of 1 to 8 carbon atoms;

$-N=CH-R^6$ $$-\underset{R^7}{\overset{}{\underset{|}{N}}} - \overset{}{\underset{}{C}} - R\,;$$

$$-\underset{R^7}{\overset{}{\underset{|}{N}}} - \overset{S}{\overset{\|}{C}} - \underset{R^8}{\overset{}{\underset{|}{N}}} - R^6\,;$$

$$-\underset{R^7}{\overset{}{\underset{|}{N}}} - \overset{S}{\overset{\|}{C}} - \underset{R^8}{\overset{}{\underset{|}{N}}} - (NH)_{n'} - Y - R^6\,;$$

$$-\underset{R^7}{\overset{}{\underset{|}{N}}} - \overset{S}{\overset{\|}{C}} - \underset{R^8}{\overset{}{\underset{|}{N}}} - \overset{}{\underset{\overset{\|}{O}}{\overset{}{P}}} \diagup_{R^{10}}^{R^9} \text{ or}$$

$$-\underset{R^7}{\overset{}{\underset{|}{N}}} - \overset{S}{\overset{\|}{C}} - \underset{R^8}{\overset{}{\underset{|}{N}}} - \overset{}{\underset{\overset{\|}{O}}{\overset{}{C}}} - OR^{11}$$

wherein $R^6$ is an aliphatic moiety of 1 to 8 carbon atoms or phenyl;

$R^7$ and $R^8$ are each hydrogen, alkyl of 1 to 4 carbon atoms, haloalkyl of 1 to 4 carbon atoms, cycloalkyl of 5 or 6 carbon atoms, alkoxyalkyl of 2 to 6 carbon atoms, cyanoalkyl of 1 to 4 carbon atoms, alkenyl of 3 or 4 carbon atoms, haloalkenyl of 3 or 4 carbon atoms, alkynyl of 3 or 4 carbon atoms haloalkynyl of 3 or 4 carbon atoms, benzyl or phenyl;

$R^9$ is R", OR", N(R")$_2$ or SR"; and $R^{10}$ is R", N(R")$_2$ or SR$_2$ wherein R" is an aliphatic moiety of 1 to 8 carbon atoms or phenyl provided that $R^9$ and $R^{10}$ are not simultaneously R";

$R^{11}$ is alkyl of 1 to 8 carbon atoms or phenyl; n' is zero or 1; and

Y is carbonyl, sulfinyl or sulfonyl.

2. A compound according to claim 1 of the formula:

$$\underset{R^{15}-A}{\overset{}{\underset{Z'}{\diagdown}}} NH - \overset{S}{\overset{\|}{C}} - NH - \overset{O}{\overset{\|}{P}} \overset{R^{13}}{\underset{R^{14}}{\diagup}} \quad \text{IV}$$

wherein A is pyridinylene;

$R^{13}$ and $R^{14}$ are the same or different and are each selected from the group consisting of OR$_1$', N(R$_1$')$_2$ and SR$_1$' wherein R$_1$' is alkyl of 1 to 4 carbon atoms, alkoxyalkyl of 2 to 6 carbon atoms, haloalkyl of 1 to 4 carbon atoms, alkynyl of 3 or 4 carbon atoms or phenyl;

$R^{15}$ is hydrogen, alkyl of 1 to 4 carbon atoms, alkoxy of 1 to 4 carbon atoms, alkenyl of 3 or 4 carbon atoms, halo, nitro, carboxy, benzoyl, phenylthio, phenylsulfinyl or phenylsulfonyl;

$Z^1$ is

wherein $R^{16}$ is hydrogen, alkyl of 1 to 6 carbon atoms, haloalkyl of 1 to 6 carbon atoms, alkenyl of 3 to 6 carbon atoms, alkoxyalkyl of 2 to 8 carbon atoms, benzyl or phenyl;

—N=CHR$^{6'}$;

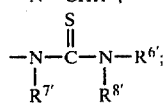

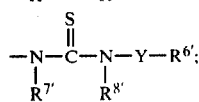

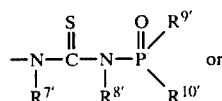

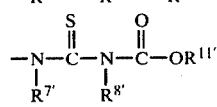

wherein $R^{6'}$ is alkyl of 1 to 4 carbon atoms, haloalkyl of 1 to 4 carbon atoms, benzyl or phenyl;

$R^{7'}$ and $R^{8'}$ are each selected from the group consisting of hydrogen alkyl of 1 to 4 carbon atoms, alkenyl of 3 or 4 carbon atoms, alkoxyalkyl of 2 to 4 carbon atoms and benzyl;

$R^{9'}$ is $OR_1''$, $SR_1''$ or $N(R_1'')_2$ and $R^{10'}$ is $SR_1''$ or $N(R_1'')_2$ wherein $R_1''$ is alkyl of 1 to 4 carbon atoms, alkoxyalkyl of 2 to 6 carbon atoms, haloalkyl of 1 to 4 carbon atoms, alkenyl of 3 or 4 carbon atoms or phenyl;

$R^{11'}$ is alkyl of 1 to 8 carbon atoms or phenyl; and

Y is carbonyl or sulfonyl.

3. A compound according to claim 1 wherein A is

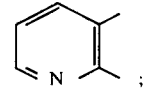

Z is NH$_2$; and $R^1$ and $R^2$ are each ethoxy.

4. An anthelmintic composition for oral administration comprising an effective amount of a compound of claim 3 and a pharmaceutically acceptable carrier.

5. A method for combating a helminth infection in a host animal which comprises administering an effective amount of a compound of claim 3.

6. An anthelmintic composition for oral administration comprising an effective amount of a compound of claim 1 and a pharmaceutically acceptable carrier.

7. An anthelmintic composition for oral administration comprising an effective amount of a compound of claim 2 and a pharmaceutically acceptable carrier.

8. The composition of claim 6 in tablet form.

9. The composition of claim 7 in liquid form.

10. The method for combatting a helminth infection in a host animal which comprises administering an effective amount of a compound of claim 1.

11. The method for combatting a helminth infection in a host animal which comprises administering an effective amount of a compound of claim 2.

* * * * *

Disclaimer

4,170,648.—*Ronald P. Owen,* Warminster and *George Miller,* Glenside, Pa. and *Charles M. Schneider,* Cullowhee, N.C. PHOSPHONOTHIOUREIDE ANTHELMINTICS. Patent dated Oct. 9, 1979. Disclaimer filed Mar. 31, 1981 by the assignee, *Beecham, Inc.*

Hereby enters this disclaimer to all of the claims of said patent.
[*Official Gazette December 15, 1981.*]